United States Patent [19]

Figler et al.

[11] Patent Number: 4,647,219

[45] Date of Patent: Mar. 3, 1987

[54] SAFETY SYSTEM FOR HEATING CONDUIT

[75] Inventors: Alan A. Figler, Algonquin; Daniel J. Grimm; Leonard F. Goloski, both of McHenry; James P. Martucci, Palatine, all of Ill.

[73] Assignee: Baxter Travenol Laboratories, Inc., Deerfield, Ill.

[21] Appl. No.: 818,381

[22] Filed: Jan. 9, 1986

Related U.S. Application Data

[63] Continuation of Ser. No. 547,238, Oct. 31, 1983, abandoned.

[51] Int. Cl.[4] ............ G01K 13/00; G01M 19/00
[52] U.S. Cl. ............................ 374/1; 374/102; 374/148; 128/202.22; 128/203.27; 128/204.17; 340/588; 340/686
[58] Field of Search ............ 73/1 R; 374/1, 148, 374/102; 128/736, 202.22, 205.23, 203.27, 204.17; 364/580; 236/DIG. 8, 94; 237/81, 12; 340/501, 514, 516, 527, 529-530, 588-589, 635, 653, 686, 687

[56] References Cited

U.S. PATENT DOCUMENTS

| | | | |
|---|---|---|---|
| 3,594,788 | 7/1971 | Seelig | 340/530 X |
| 3,741,476 | 6/1973 | Travaglio | 374/1 X |
| 3,902,351 | 9/1975 | Kreps | 374/1 |
| 3,970,929 | 7/1976 | Borucki et al. | 340/514 X |
| 4,115,998 | 9/1978 | Gilbert et al. | 374/1 X |
| 4,214,237 | 7/1980 | Zissimopoulos | 340/686 |
| 4,331,161 | 5/1982 | Patel | 128/736 |
| 4,399,823 | 8/1983 | Donnelly | 128/736 |
| 4,399,824 | 8/1983 | Davidson | 128/736 |
| 4,564,748 | 1/1986 | Gupton | 128/203.27 X |
| 4,586,149 | 4/1986 | Stillman et al. | 128/736 X |

FOREIGN PATENT DOCUMENTS

| | | | |
|---|---|---|---|
| 114566 | 9/1979 | Japan | 374/1 |
| WO79/00691 | 9/1979 | PCT Int'l Appl. | 340/588 |
| 2061495 | 5/1981 | United Kingdom | 128/736 |
| 561093 | 6/1977 | U.S.S.R. | 374/1 |

OTHER PUBLICATIONS

"Mich Humidity Center Operation & Maintenance Instructions"; Form No. 39-00-1000; Oct. 1981; 8 pages; Chemetron Medical Division, Allied Health Care Products, Inc.
Servo Temperature-Humidity Controller; Servo-Pak III; 2 page advertisement; by Sep. 1982.
RCI Installation and Instruction Manual for Conchatherm III Humidifier before Oct. 31, 1983.
Operating Instructions for Cascade II Humidifier, Form 9188A, Mar. 1977.

Primary Examiner—Stewart J. Levy
Assistant Examiner—Tom Noland
Attorney, Agent, or Firm—Paul C. Flattery; George H. Gerstman; Kay H. Pierce

[57] ABSTRACT

A process is provided for detecting if a temperature sensor (18) is correctly located in a heating conduit at a point that is remote from the heater (28). Power is applied to the heater (28) in a predetermined manner. The change in the temperature sensed by the temperature sensor (18) is observed. If the temperature sensed by the temperature sensor (18) has changed in a certain manner, a signal is provided indicating that the temperature sensor (18) is located correctly. If, during observation, the temperature sensed has not changed in the certain manner, an alarm signal is provided.

12 Claims, 12 Drawing Figures

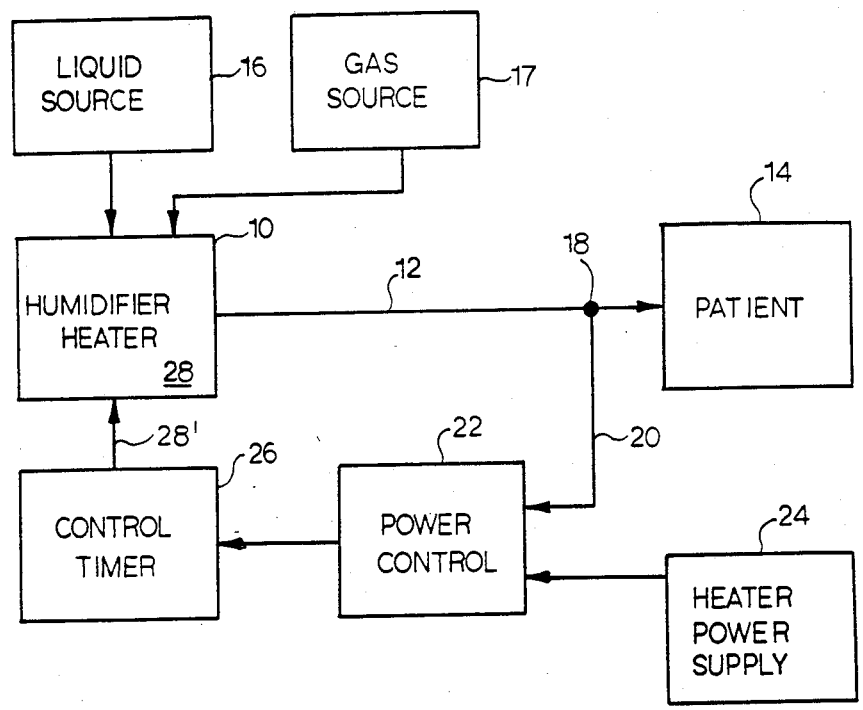
FIG. 1
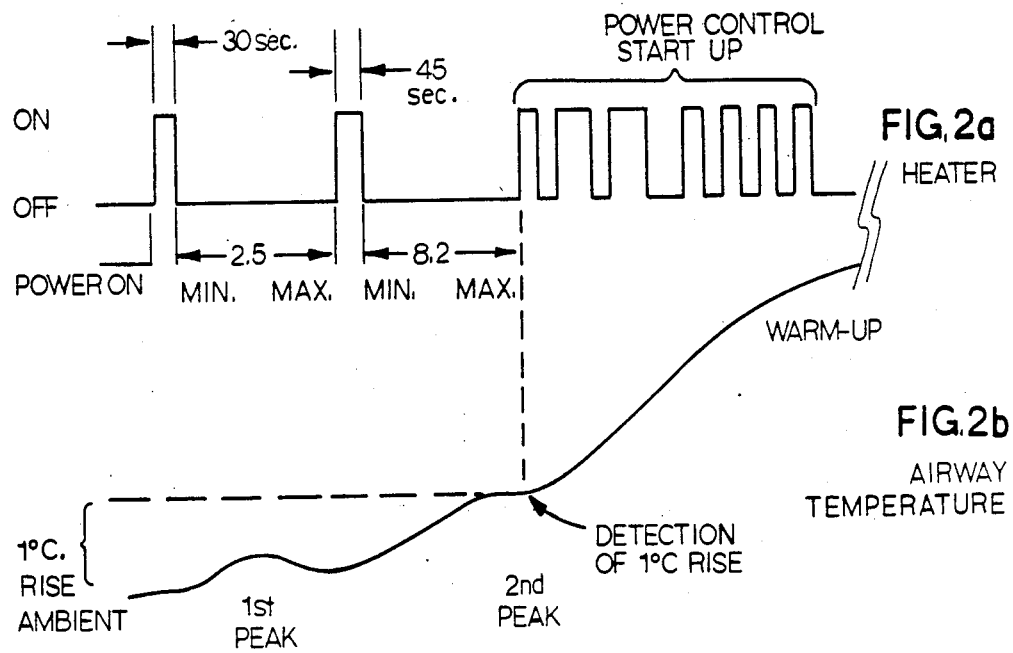
FIG. 2a
FIG. 2b

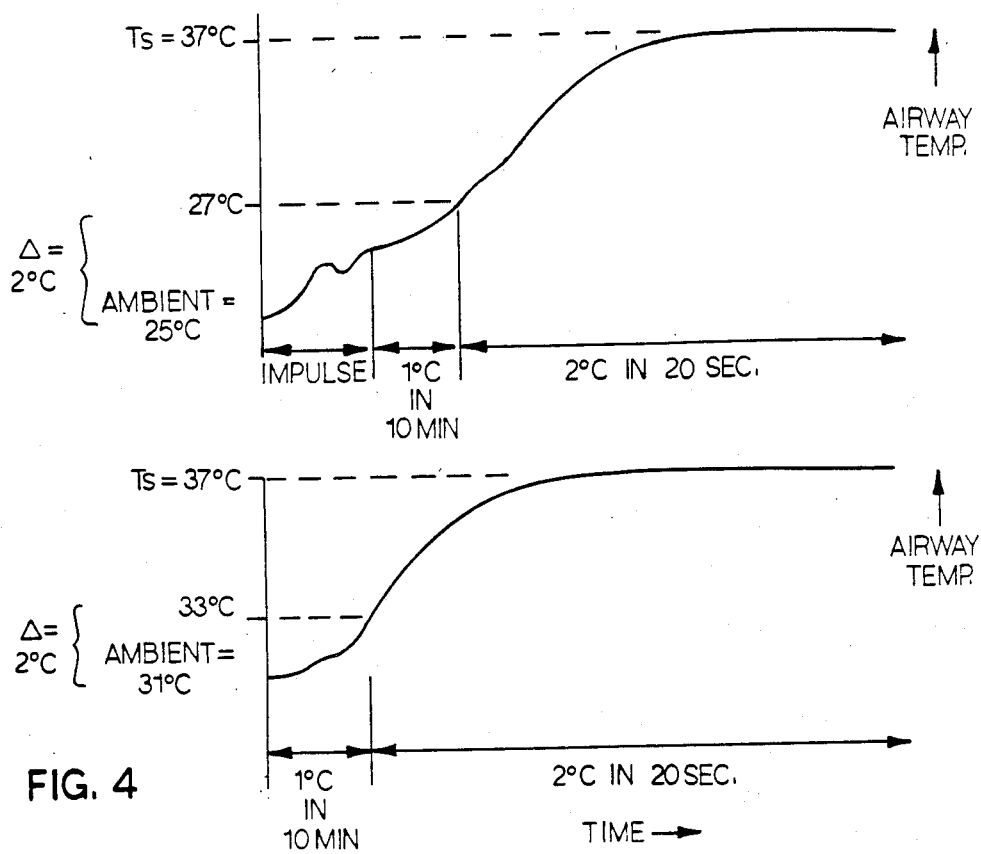
FIG. 3
FIG. 4
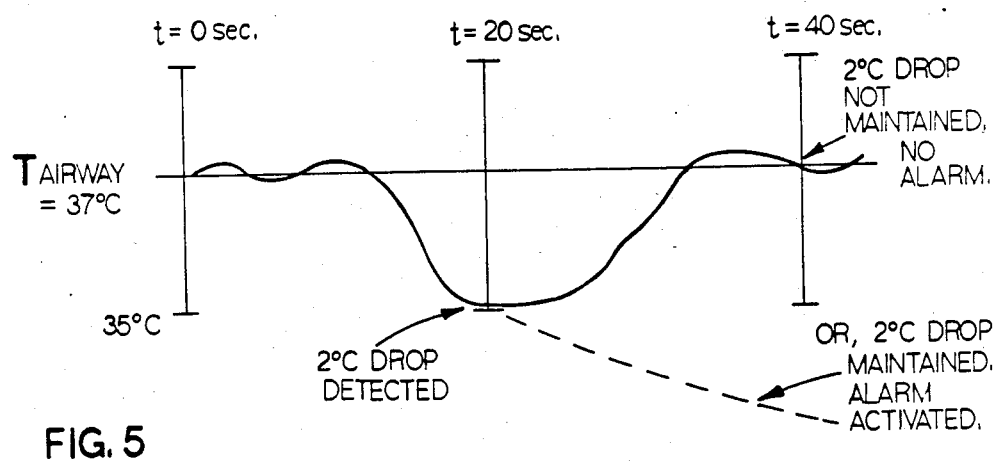
FIG. 5

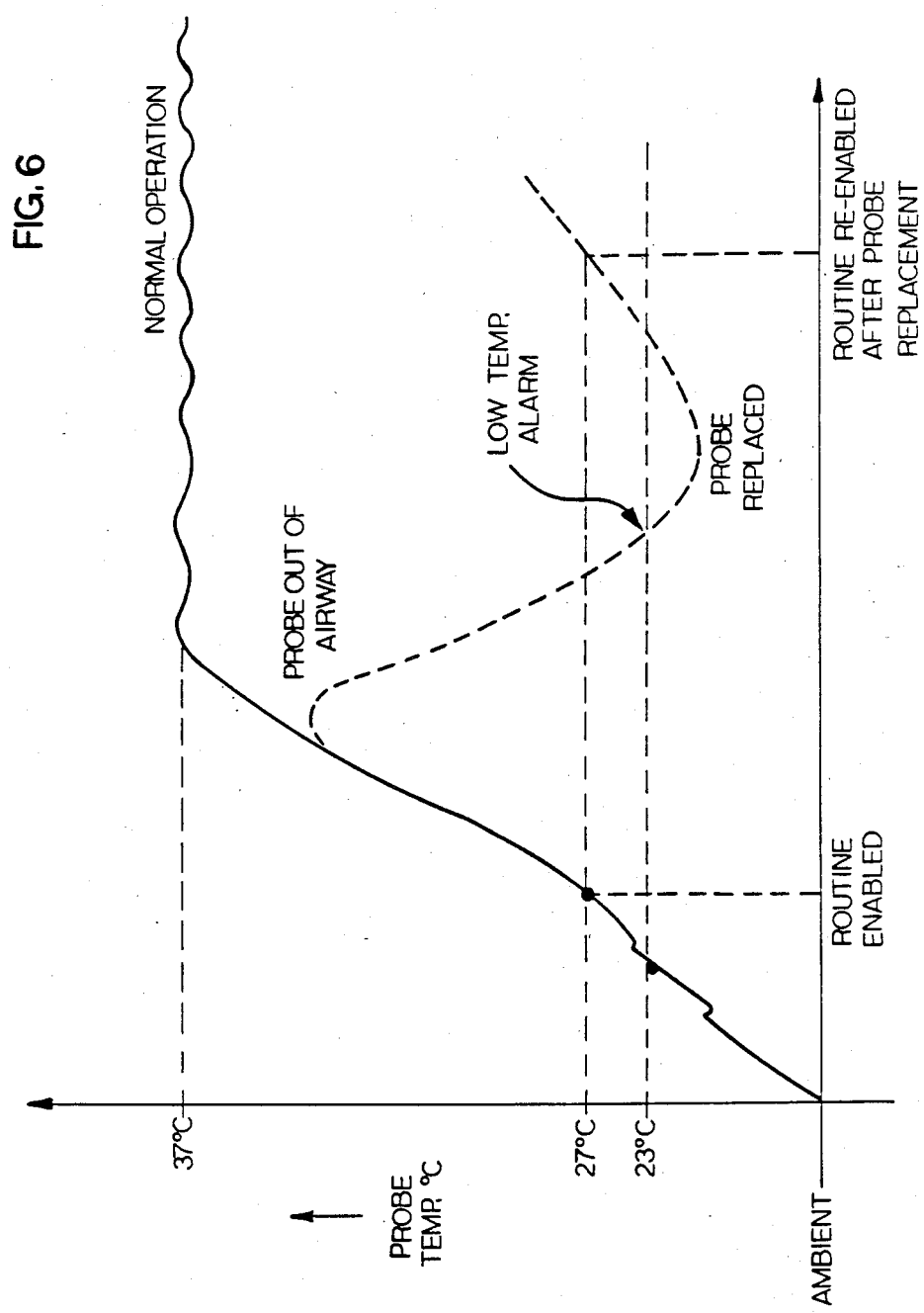

SAFETY SYSTEM FOR HEATING CONDUIT

This application is a continuation of application Ser. No. 547,238, filed Oct. 31, 1983 now abandoned.

TECHNICAL FIELD

The present invention concerns a novel process for detecting if a temperature sensor is correctly located in a heating conduit at a point that is remote from the heater.

BACKGROUND ART

In U.S. Pat. No. 4,303,601, entitled "Ventilator-Humidifier," there is disclosed a system for providing humidified air or other gas to a patient. Air or other gas is directed to the humidifier where the gas is saturated by the humidifier. The saturated gas is fed through tubing which extends to the patient. The airway temperature of the humidified gas (at the airway opening adjacent the patient's mouth) is different from the temperature of the gas adjacent to the humidifier. A temperature probe is provided adjacent the airway opening for feedback control of the temperature.

It is important that the temperature probe be located correctly adjacent the airway opening. Because the temperature probe is located in the tubing at a point that is remote from the heater, it is desirable to detect if the temperature probe is correctly located prior to the time that the delivered gas reaches an undesirable high temperature.

Although the illustrative embodiment concerns the detection of the presence of a temperature probe in the air delivery tubing connected to a feedback-controlled heated humidifier that is used for delivering humidified gases to a patient, it is to be understood that the present invention is applicable to the detection of any temperature sensor located in a heating conduit at a point that is remote from the heater.

Therefore, it is an object of the present invention to provide a process for detecting if the temperature sensor is correctly located in a heating conduit at a point that is remote from the heater, before the heated fluid, e.g., gas, reaches an undesirable high temperature.

Another object of the present invention is to provide a system which is operational to detect if the temperature sensor has been removed from a heating conduit during operation of the system.

Other objects and advantages will become apparent as the description proceeds.

DISCLOSURE OF THE INVENTION

In accordance with the present invention, a process is provided for detecting if a temperature sensor is correctly located in a heating conduit at a point that is remote from the heater. The process comprises the steps of applying a predetermined amount of power to the heater for a predetermined amount of time, observing the change in the temperature sensed by the temperature sensor and providing a signal that the temperature sensor is located correctly if the temperature sensed by the temperature sensor has risen at least a predetermined amount.

In an illustrative embodiment, if during observation the temperature sensed has not risen at least a predetermined amount, then a second predetermined amount of power is applied for a second predetermined amount of time. The change in the temperature sensed by the temperature sensor is again observed. If the temperature sensed by the temperature sensor has risen at least a predetermined amount, a signal is generated indicating that the temperature sensor is located correctly. If the temperature sensed has not risen at least a predetermined amount after the second application of power, an alarm signal is provided.

In an illustrative embodiment, means are provided for detecting if the temperature sensed is at least a second predetermined amount below a selected set point. If the temperature sensed is at least a second predetermined amount below the selected set point, then a timer is set for a selected amount of time. The change in the temperature sensed during the selected amount of time is observed and an alarm signal is provided if the temperature sensed has not risen at least a third predetermined amount during the selected amount of time.

In an illustrative embodiment, the second predetermined amount is between 3° C. and 4° C. and the third predetermined amount is about 1° C.

In an illustrative embodiment, the sensed temperature is stored. Means are provided for detecting if the temperature sensed has dropped at least a fourth predetermined amount within a third predetermined time period. If the temperature sensed has dropped at least a fourth predetermined amount within the third predetermined time period, then it is determined if the temperature drop is maintained or exceeded during a fourth predetermined time period after the temperature drop is detected. An alarm signal is provided if the temperature drop is maintained or exceeded during the fourth predetermined time period.

In an illustrative embodiment, it is determined whether the probe temperature has reached a first predetermined temperature. If the probe temperature has reached the first predetermined temperature, it is thereafter determined if the probe temperature has fallen to a second predetermined temperature, with the second predetermined temperature being a lower temperature than the first predetermined temperature. If the probe temperature has fallen to the second predetermined temperature, an alarm signal is provided. However, if the temperature has not reached the first predetermined temperature, then power is continued to be applied to the heater to increase the temperature and there is a continuing determination if the probe temperature has reached the first predetermined temperature. In this manner, once the first predetermined temperature is reached an alarm signal will be provided if the probe temperature falls to the second predetermined temperature that is below the first predetermined temperature. The difference between the first predetermined temperature and the second predetermined temperature gives sufficient hysteresis to prevent nuisance alarms.

A more detailed explanation of the invention is provided in the following description and claims, and is illustrated in the accompanying drawings.

BRIEF DESCRIPTION OF THE DRAWINGS

FIG. 1 is a block diagram of a humidifier temperature control system of the type with which the process of the present invention is intended to operate.

FIG. 2A is a time versus power graph of the power applied to the heater in accordance with the process of the present invention.

FIG. 2B is a time versus temperature graph of the temperature detected by the temperature probe, in coordination with the time versus power graph of FIG. 2A.

FIG. 3 is a time versus temperature graph showing one possible temperature sensing operation by the temperature probe.

FIG. 4 is a time versus temperature graph showing another possible temperature sensing operation by the temperature probe.

FIG. 5 is a time versus temperature graph showing a possible sensed probe temperature.

FIG. 6 is a time versus temperature graph showing further temperature sensing operation by the temperature probe.

DETAILED DESCRIPTION OF THE ILLUSTRATIVE EMBODIMENT

Figure 7A:
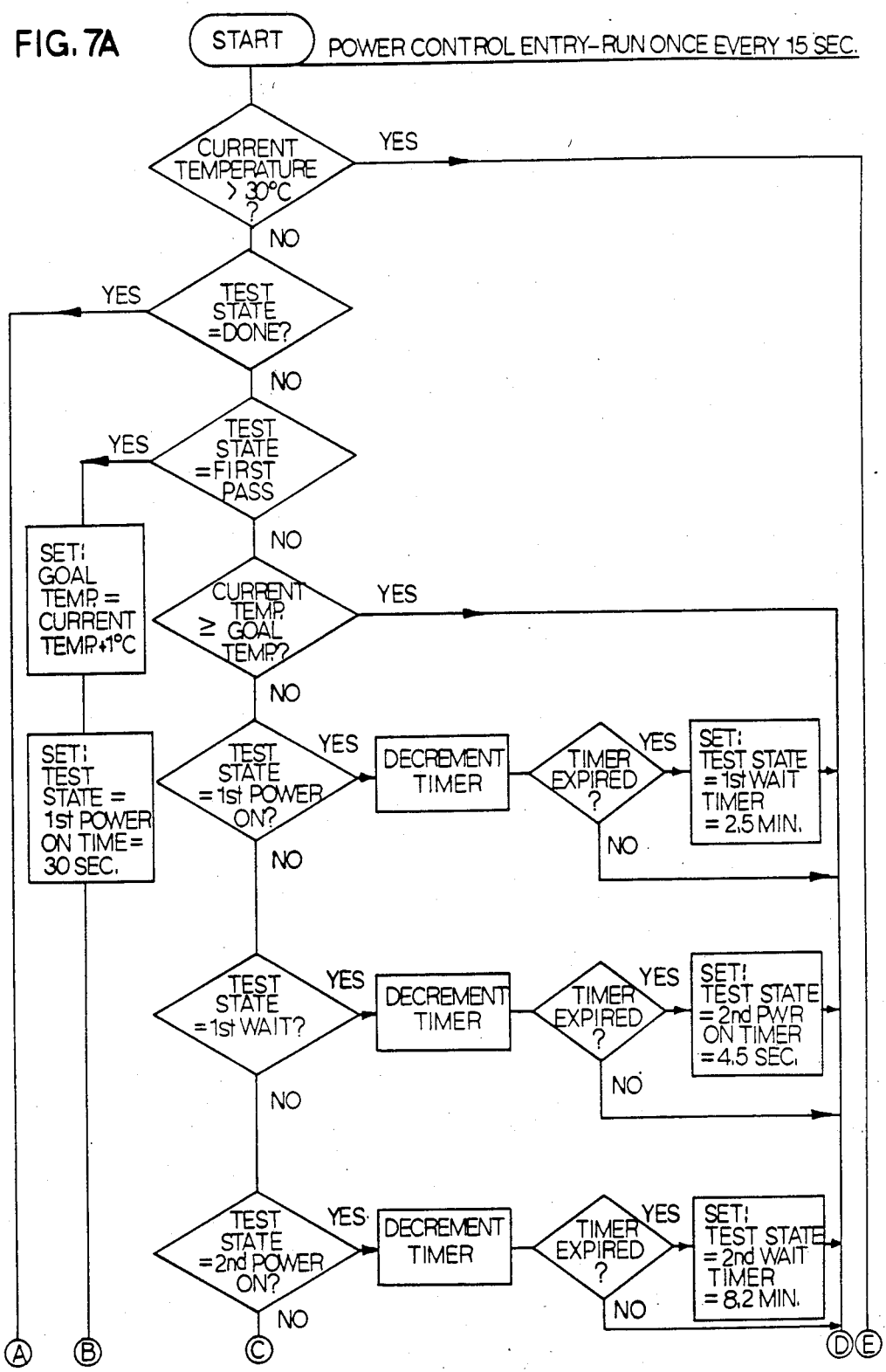
FIG. 7A and FIG. 7B, when taken together, form a flow diagram of an impulse process for detecting if a temperature sensor is correctly located in the heating conduit.

Referring to FIG. 1, a humidifier 10 with a heater has a humidified gas outlet tube 12 coupled to a patient 14 with tube 12 typically terminating at a tracheal tube. Humidifier 10 is supplied with appropriate liquid, such as sterile water, from liquid source 16, and with appropriate gas, such as an oxygen-air mixture, from gas source 17. The temperature of the humidified gas adjacent the patient's mouth and nose, preferably the "airway" temperature, is sensed by means of a thermistor 18 which provides a signal via line 20 to power control system 22. The power control system 22 includes an analog to digital converter which receives an analog signal from the thermistor 18 which provides a signal via line 20 to power control system 22. The power control system 22 includes an analog signal from the thermistor 18 and provides pulses proportional to the analog signal to a microprocessor.

The voltage supply 24 for the humidifier-heater is controlled in accordance with the power control system 22. In the illustrative embodiment, the humidifier uses a fixed resistance heater 28 and the power control system 22 is operative to actuate a heater control timer 26. Timer 26 applies the supply voltage 24 to the heater 28 for a fractional portion of a selected sensing period. In this manner, the fixed resistance heater within humidifier 10 is effectively operating for only a fraction of the sensing period, with a fraction determined by a microprocessor which reads the airway temperature sensed by thermistor 18.

A detailed description of the microprocessor-based control system for the heater 28 of humidifier 10 is disclosed in United States application Ser. No. 383,113, filed May 28, 1982, entitled "Temperature Controlled Process," and assigned to the assignee of the present invention.

In accordance with the present invention, a process is provided for detecting if thermistor 18 is correctly located in the airway tube 12. In the specification and drawings, the term "POA" will sometimes be used to represent the testing accomplished by the process of the present invention, with "POA" meaning "probe out of airway" and thereby referring to the detection of the temperature probe being out of the airway tube.

Now referring to FIG. 2A, this Figure shows the power on line 28' (FIG. 1) being applied to the humidifier-heater over a period of time. Once the power is turned on, for ambient temperatures of 30° C. and below, one or two pulses of 100 percent power are applied to heater 28 in order to verify that the remote temperature probe 18 is correctly placed in the airway 12. It can be seen that when the power commences, 30 seconds of full power is applied to heater 28, followed by a 2.5 minute of observation to determine whether there has been a 1° C. rise in airway temperature. If a 1° C. (or greater) rise in airway temperature is detected, the power control system 22 operates to provide the normal warm-up curve, designated "power control start-up" in FIG. 2A. On the other hand, if the 1° C. criterion is not satisfied at the end of the 2.5 minute interval, 45 seconds of full power is applied, followed by an 8.2 minute period of observation to determine if there has been a 1° C. (or greater) rise.

The temperature curve is illustrated in FIG. 2B. When power is turned on initially, the probe is at ambient temperature. In FIG. 2B, during the first 2.5 minute observation interval, there has not been a 1° C. rise and thus the 45-second application of power is utilized. Prior to the end of the 8.2 minute observation interval, the probe detects a 1° C. rise and the power control start-up commences.

Two applications of power are used because of the differences between the response of pediatric airway tubing and adult airway tubing. The 30-second power application is sufficient to detect the temperature probe in place in the pediatric circuit for flow rates of 4 to 25 LPM without producing an unacceptable rise in gas temperature, and the combination of the 30-second and 45-second applications is sufficient to detect the probe in place in the adult airway tube under flow conditions from 4 to 60 LPM.

It can be seen that once the 1° rise of temperature is detected during one of the observational intervals, a signal is provided to the power control system indicating that the temperature probe is located correctly and the power control system then commences its start-up procedure. If the temperature sensed has not risen at least 1° C. during one of the observation intervals, an alarm signal is provided indicating a POA (probe out of airway) condition. Another process for detecting if the temperature sensor is correctly located in the airway tube is illustrated in FIGS. 3 and 4. Referring to FIGS. 3 and 4, it can be seen that a temperature set point $T_s$ is 37° C. When the probe temperature is 4° C. or more below this set point, a probe alarm will be activated if the probe temperature does not rise at least 1° C. in each 10-minute interval. In FIG. 3, the ambient temperature is 25° C. The first portion of the graph (designated "impulse") corresponds to the impulse test of FIGS. 2A and 2B. Once the impulse test is passed, so long as the probe temperature is 4° C. or more below set point (i.e., 33° C. or below) the probe temperature will be observed every 10 minutes to determine whether there has been at least a 1° C. rise in temperature. It can be seen that in the second interval, there has been a 1° C. rise within the 10-minute time interval and thus the probe alarm will not be activated. The 1° C. rise per 10-minute time period has continued and the temperature finally reached 37° C. without the probe alarm being activated in FIG. 3.

In FIG. 4, the ambient temperature is 31° C. and it can be seen that the temperature has risen at a rate of at least 1° C. per 10-minute time interval, thereby preventing the probe alarm from being activated.

Thus if the temperature sensed is more than a predetermined amount (e.g., 4° C.) below a selected set point (e.g., 37° C.), then a timer is set for a selected amount of time (e.g., 10 minutes). The change in the temperature is sensed during the selected amount of time and an alarm signal is provided if the temperature sensed has not risen at least a second predetermined amount (e.g., 1° C.) during the selected amount of time.

If the temperature sensed has risen at least 1° C. within the selected 10-minute time interval, then the sensed temperature is stored and the process is repeated for another 10-minute time interval until the temperature is within 4° from the set point.

Another process is utilized for detecting if the temperature sensor is correctly located in the airway tube, comprising the detection of the probe temperature decreasing 2° C. or more in a 20-second time period. To this end, the sensed temperature is stored and means are provided for detecting if the temperature sensed has dropped at least a first predetermined amount (e.g., 2° C.) within a first predetermined time period (e.g., 20 seconds). If the temperature sensed has dropped at least the first predetermined amount within the first predetermined time period, then means are provided for determining if the temperature drop is maintained or exceeded during a second predetermined time period (e.g., 20 seconds) after the temperature drop is detected. An alarm signal is provided only if the temperature drop is maintained or exceeded during the second predetermined time period.

The aforementioned process is illustrated in FIG. 5 in which the airway temperature is 37° C. During a first predetermined time period of 20 seconds, a 2° C. drop is detected. However, if the probe alarm will not be activated but instead the probe temperature will be detected for another 20-second time period. As shown in the full line, since the 2° C. drop was not maintained during the second 20-second time period, an alarm is not provided. However, as shown in the dashed line representation, if the 2° C. drop were maintained during the second time period, the alarm would be activated.

Previously in connection with FIGS. 3 and 4, it was discussed how the probe temperature will be observed every 10 minutes to determine whether there has been at least a 1° C. rise in temperature. So long as the probe temperature is below a set point and there has been a 1° rise within a 10-minute time interval, the probe alarm will not be activated. However, this routine requires that a first 10-minute interval be observed and even if the rise does not occur during that first 10-minute interval, a second 10-minute interval must be observed. In FIG. 6, another routine is disclosed for determining if the probe is out of the airway, but without requiring a 10-minute observation time in order to make the determination. Referring to FIG. 6, the full line representation shows power being applied to the heater and the airway temperature increases. Once the airway temperature reaches a first predetermined temperature, for example, 27° C., a determination is made whether the airway temperature thereafter falls to a second predetermined temperature, for example, 23° C., with the second predetermined temperature being lower than the first predetermined temperature in order to provide sufficient hysteresis to prevent nuisance alarms. In FIG. 6, the full line representation shows normal operation wherein the power is applied and the airway temperature reaches its normal heated temperature of 37° C. The dashed line representation shows an abnormal condition, such as the probe being out of the airway. In this manner, it is seen that the temperature begins to drop after it has reached 27° C. and it continues to drop until a low temperature alarm is provided at the second predetermined temperature which is 23° C. in this illustrative embodiment.

By using the aforementioned routine during warm-up, an extensive amount of time is not required to determine if the probe is out of the airway. There is simply a determination as to whether the temperature has dropped below a second predetermined temperature which is below the first predetermined temperature at which the routine begins.

Figure 7B:
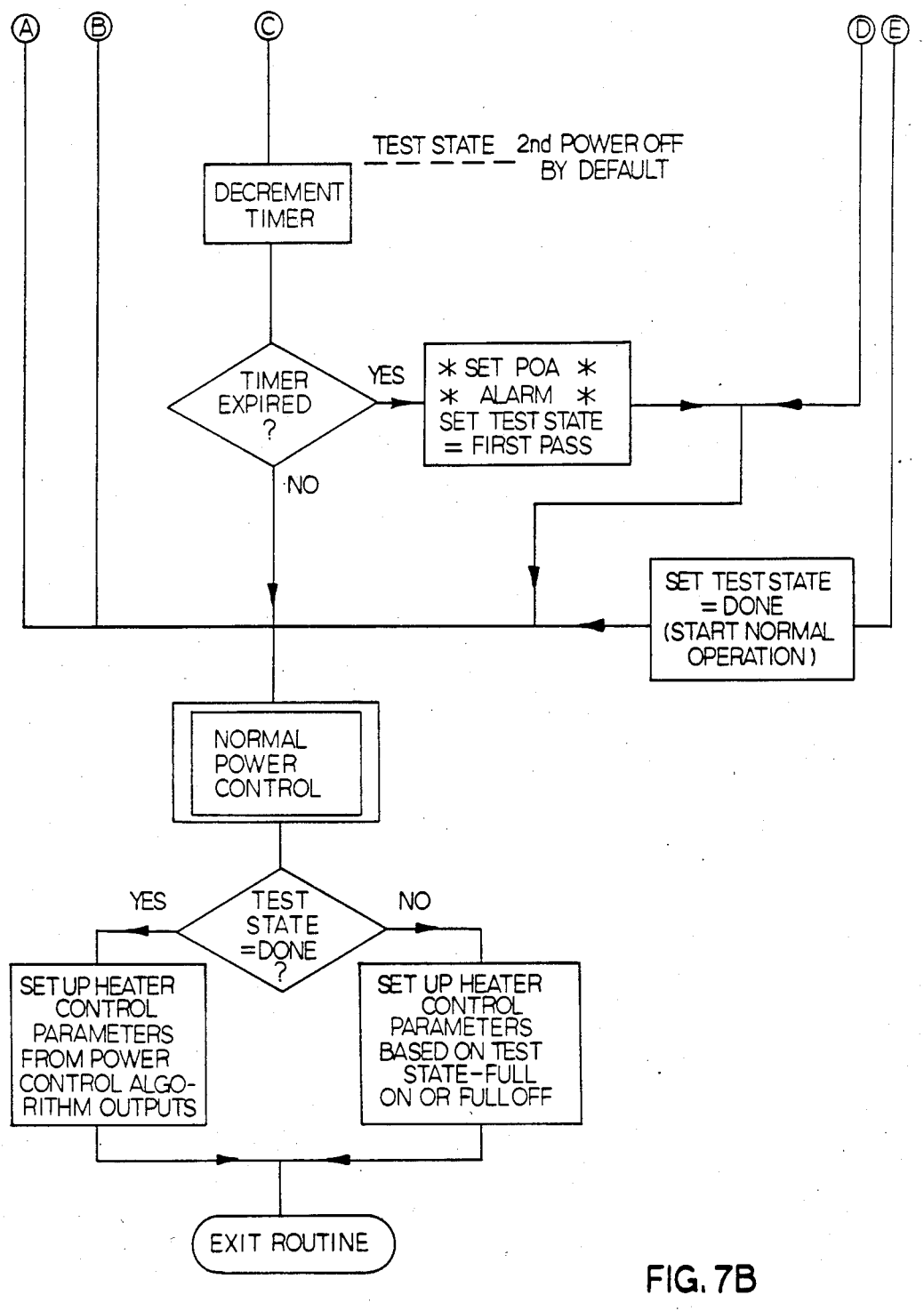

Referring to FIGS. 7A and 7B, a flow diagram is provided for illustrating the steps of the process of the present invention relating to the impulse test of FIGS. 2A and 2B.

Figure 8:
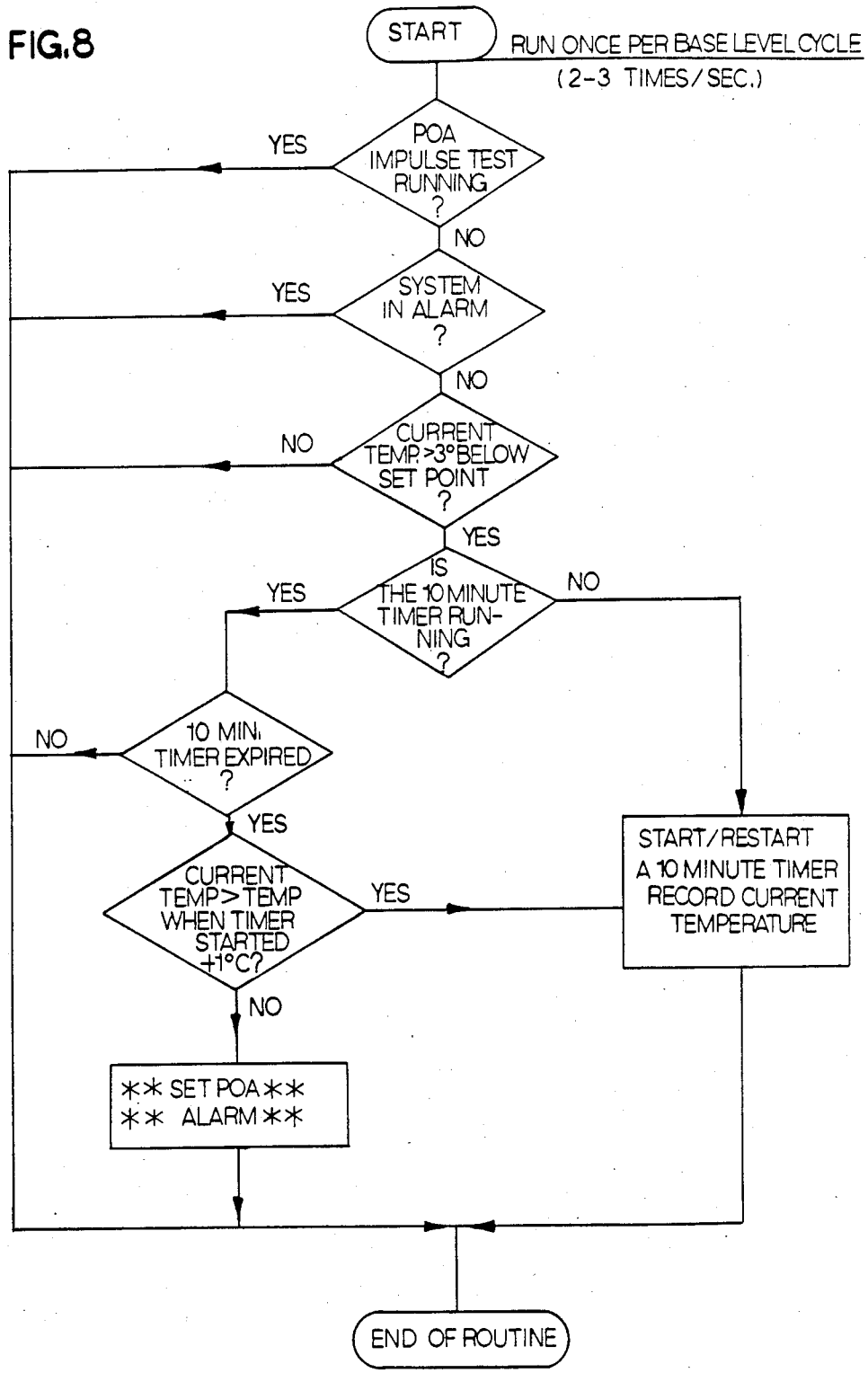
FIG. 8 is a flow diagram illustrating another process in accordance with the principles of the present invention.

In FIG. 8, a flow diagram is provided for illustrating the steps of the process of the present invention relating to the process of FIGS. 3 and 4, in which a probe alarm will be activated if the probe temperature does not rise at least a predetermined amount within a selected time period.

Figure 9:
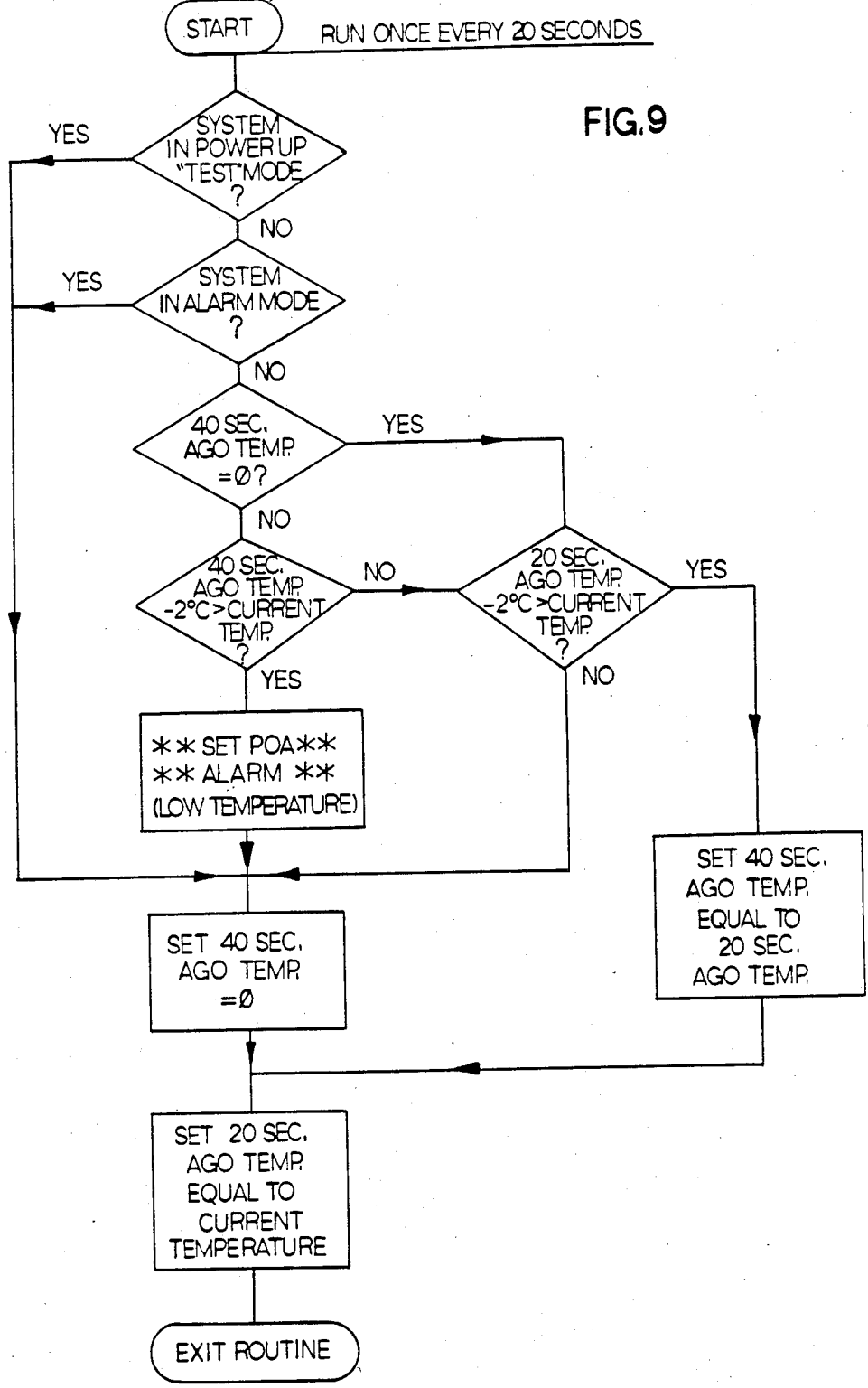
FIG. 9 is a flow diagram illustrating still another process according to the principles of the present invention.

In FIG. 9, a flow diagram is provided for illustrating the steps of the process of the present invention in connection with the FIG. 5 embodiment, in which the probe alarm will be activated if the probe temperature decreases a predetermined amount or more within a selected time period and the decrease is maintained during a second selected time period.

Figure 10:
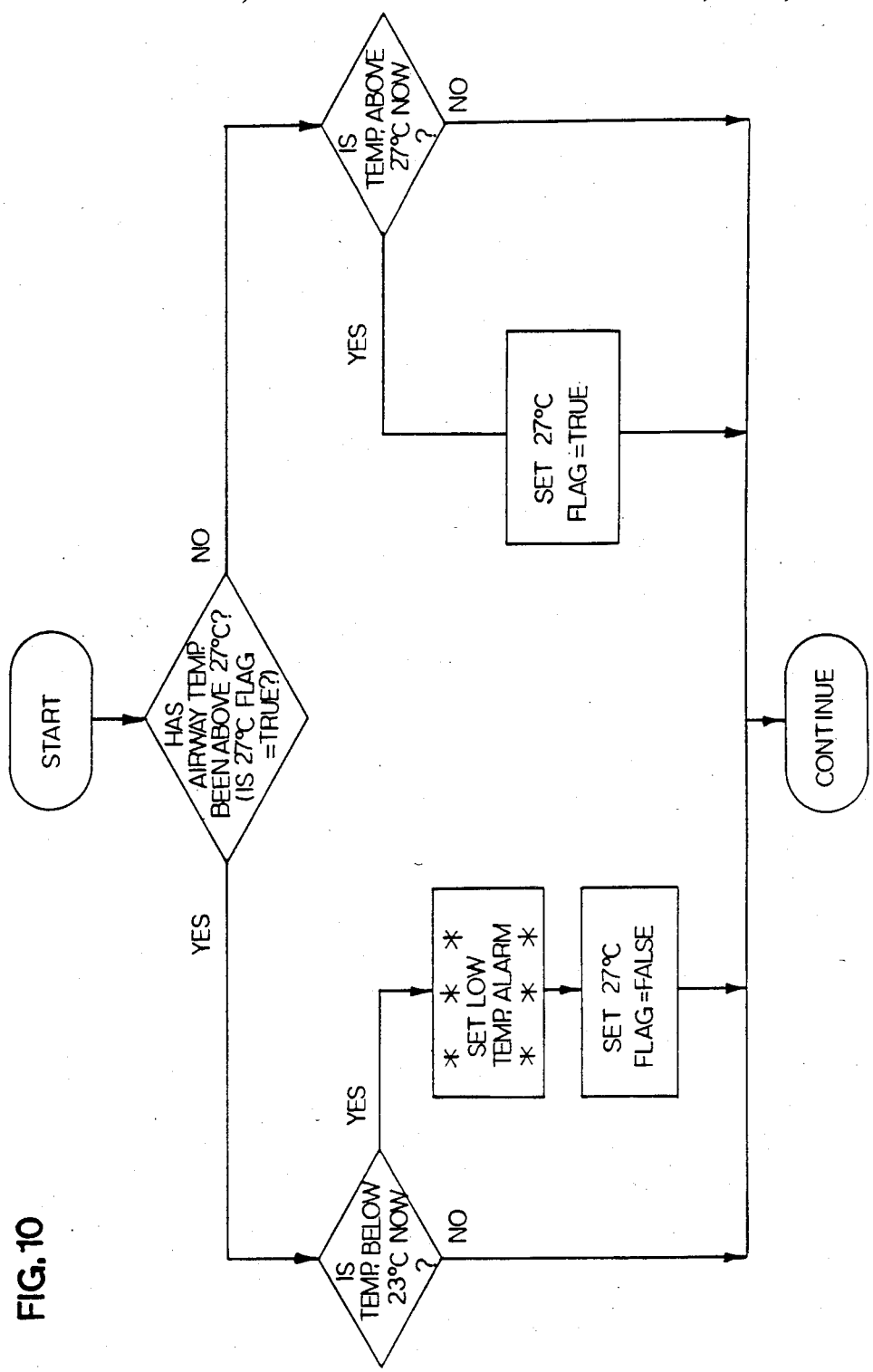
FIG. 10 is a flow diagram illustrating an additional process according to the principles of the present invention.

In FIG. 10, a flow diagram is provided illustrating the steps of the process of the present invention in connection with the FIG. 6 embodiment, in which the probe alarm will be activated if the probe temperature falls to a second predetermined temperature that is lower than a first predetermined temperature which is reached shortly after warm-up. Although in the FIGS. 6 and 10 embodiment the first predetermined temperature is 27° C. and the second predetermined temperature is 23° C., it is understood that these temperatures are examples only and may be varied as desired.

The process steps described and illustrated in the flow diagrams of FIGS. 7A, 7B, 8, 9 and 10 can be achieved using copyrighted computer programs, ©1983 by Travenol Laboratories, Inc., which are presented in detail below. Although illustrative embodiments of the invention are described herein, it is to be understood that various modifications and substitutions may be made by those skilled in the art without departing from the spirit and scope of the present invention.

The following assembly language problems and hexidecimal code comprises register definitions embodied in a 2K×8 E PROM operable with a MOSTEK F8 microprocessor:

```
NLIST
SUBTTL  DEFINITIONS FOR THE HLLC
FORMLN  48
@Copyright 1983 - Travenol Laboratories, Inc CLPSMU  EQU  2         Tube Clamp Sample Counter
CLPSML  EQU  0

MS100U  EQU  2         100 Msec Timer
MS100L  EQU  1

FPDCTU  EQU  2         Front Panel Sample Counter
FPDCTL  EQU  2

DETDCU  EQU  2         Heater Sensor Counter
DETDCL  EQU  3

HTVSMU  EQU  2         Heater Sensor Sample Counter
HTVSML  EQU  4

MINFLU  EQU  2         Minimum Flow Timer
MINFLL  EQU  5

CLK1U   EQU  2         Two & a Half (2.5) Second Timer
CLK1L   EQU  6

MAXFLU  EQU  2         Maximum Fill Timer
MAXFLL  EQU  7

ACSTMU  EQU  3         High Temperature Silence Timer
ACSTML  EQU  0

LTTMU   EQU  3         Water Level Drive Timer
LTTML   EQU  1

LTFLGU  EQU  3         Flags
LTFLGL  EQU  2

FPSTNU  EQU  3         Front Panel Sample Register
FPSTNL  EQU  3

FPSTPU  EQU  3         Front Panel Status Register
FPSTPL  EQU  4

DETSNU  EQU  3         Detector Sample Register
DETSNL  EQU  5

DETSTU  EQU  3         Detector Status Register
DETSTL  EQU  6

SOLDRU  EQU  3         Tube Clamp Status Register
SOLDRL  EQU  7

LEDU    EQU  4         LED Display Register
LEDL    EQU  0

TMSDU   EQU  4         Temperature Display MSD
TMSDL   EQU  1

TLSDU   EQU  4         Temperature Display LSD
TLSDL   EQU  2

DISPTU  EQU  4         Display Pointer
DISPTL  EQU  3

ATMRU   EQU  4         Alarm on Timer
ATMRL   EQU  4

ADSTRU  EQU  4         A/D Start Flag
ADSTRL  EQU  5

ADCNTU  EQU  4         A/D Counter
ADCNTL  EQU  6

LPTMPU  EQU  4         Last Power Cycle Temperature
LPTMPL  EQU  7
TEMPU   EQU  5         A/D Temperature
TEMPL   EQU  0

ZEROU   EQU  5         A/D Zero
ZEROL   EQU  1

HPWRSU  EQU  5         Heater Status
HPWRSL  EQU  2

TSBINU  EQU  5         Temperature Set Point
TSBINL  EQU  3
```

```
TPOASU   EQU   5        Probe Out Start Temperature
TPOASL   EQU   4

POATMU   EQU   5        Probe-Out-of-Airway Timer
POATML   EQU   5

RNGFTU   EQU   5        Feed Flow Alarm Ring Current Slot Pointer

RNGFTL   EQU   6

MINCKU   EQU   5        One Minute Clock Down-counter for Feed Alarm
MINCKL   EQU   7

A11U     EQU   6        Working Register A1 - High Byte
A11L     EQU   0

A10U     EQU   6        Working Register A1 - Low Byte
A10L     EQU   1

PROPTU   EQU   6        Proportion Cycle Timer - Low Byte
PROPTL   EQU   2

TMR1U    EQU   6        Timer High Nibbles (High-Pwr On/Low Proportional)
TMR1L    EQU   3

PWRTOU   EQU   6        Power on Timer - Low Byte
PWRTOL   EQU   4

TPWR1U   EQU   6        Total Power - High Byte
TPWR1L   EQU   6

TPWROU   EQU   6        Total Power - Low Byte
TPWROL   EQU   7

A21U     EQU   7        Working Register A2 - High Byte
A21L     EQU   0

A20U     EQU   7        Working Register A2 - Low Byte
A20L     EQU   1

PROP1U   EQU   7        Proportional Term - High Byte
PROP1L   EQU   2

PROPOU   EQU   7        Proportional Term - Low Byte
PROPOL   EQU   3

PJ1U     EQU   7        Working Register PJ - High Byte
PJ1L     EQU   4

PJOU     EQU   7        Working Register PJ - Low Byte
PJOL     EQU   5

INTG1U   EQU   7        Integral Term - High Byte
INTG1L   EQU   6

INTGOU   EQU   7        Integral Term - Low Byte
INTGOL   EQU   7
```

The following are the memory definitions embodied n the E PROM:

```
*
*        Define Locations in Main Memory
*

TABLE0   EQU      H'0EC0'        Table for Temperature Display
TABLE1   EQU      H'0EA0'        Table for Setpoint RNGBAS   EQU      H'0FC0'        Initial Bias for Feed Ring Alarm
FEDRNG   EQU      H'0FC1'        Feed Alarm Ring (0FC0 - 0FC7)

POATMR   EQU      H'0FD0'        POA Downslope Timer
POATMP   EQU      H'0FD1'        POA Downslope Previous Temperature
POAOLD   EQU      H'0FD2'        POA Downslope Old Temperature PCATMR   EQU      H'0FD3'        Power Control Impulse Test Timer
PCATMP   EQU      H'0FD4'        *       *       *    -(Goal Temperature)
PCASTT   EQU      H'0FD5'        *       *       *     Test State:
*                                         0 = Normal
*                                         1 = First Wait with Power Off
*                                         2 = First Heat On
*                                         3 = Initialize
*                                         5 = Second Wait with Power Off
*                                         6 = Second Heat On
LOWACT   EQU      H'0FD6'        Absolute Low Temperature Check Active (1=Active)

*
*        Miscellanous Parameters
*

INBIAS   EQU      -(40*2/5)      Initial Additional Allowed Feed Time (sec)
MAXFED   EQU      (40*2/5)       Maximum Allowed Feed Time in an 8 Minute Window
MINCNT   EQU      (60*2/5)       Number of Ticks in a Minute for Feed Alarm POAPER   EQU      (20*2/5)       POA Downslope Period length
POADRP   EQU      (2*8)          POA Downslope temperature drop threshold PCAHON   EQU      2              POA Impulse Test First Heat On Time (15.625 sec ticks)
PCAHOF   EQU      (2*4)+2        *       *       *     First Wait Time
PCAHN2   EQU      3              *       *       *     Second Heat On Time
PCAHF2   EQU      8*4            *       *       *     Second Wait Time
PCADLT   EQU      1*8            *       *       *     Change in Temperature
PCAMTP   EQU      (30-15)*8      *       *       *     Maximum Temperature LOWARM   EQU      (27-15)*8      Temperature to Arm   Absolute Low Temp Alarm
LOWTRG   EQU      (25-15)*8           *       *  Trigger    *       *       *

LIST
```

The following assembly language program and hexidecimal code embodied in the E PROM is the impulse routine of FIGS. 2A, 2B and 7:

```
                 TITLE   PS5A
                 SUBTTL  POWER CONTROL PART A
                 FORMLN  48
        *        @Copyright 1983 - Travenol Laboratories, Inc

INTERN  PWCTLA
                 EXTERN  PWCTLB,MCOM,MCMP,MSR,MSL,MADD,MSUB,MMUL

RSECT   PS5A

*
        *        PS5A - PCTRLA
        *
        *        POWER CONTROL - PART A
        *        Pt = Pp + Pi - Pd
        *        Where:
        *        Pp = 12(Ts - Ta)
        *        Pi = SUM OF Pj, IPjI = (1/64)Pp             ITa-TsI >= 4 DEG
        *                             = (1/64)Pp[(.64/64)Pt-]  ITa-TsI < 4 DEG
        *                            >= (.171/64)Pt-  MINIMUM RESET,SIGN AS AS Pp
        *

* Note:  This module also contains the PCA/POA 'Impulse Response Test.'
*        In order to check that the Temperature probe is in the airway,
*        initially the heater will be turned on full for a specified
*        amount of time and then off until either a specified temperature
*        rise is observed or the probe reaches a maximum allowed
*        temperature, instead of running the normal algorithm. If
*        the probe does not heat up, a Probe-Out-of-Airway alarm is
*        activated.
```

```
0000'1A      PWCTLA  DI                       ; *** Disable Interrupts ***
0001'2088            LI      .LOW.(-PCAMTP)   ; Maximum POA test Temperature
0003'65              LISU    TEMPU            ; Current Temperature
0004'68              LISL    TEMPL
0005'CC              AS      S
0006'9104            BM      10$
0008'290095'         JMP     70$              ; Too Hot (probe probably in)-Abort test 000B'2A0FD5  10$     DCI     PCASTT           ; Check for POA Test Mode
000E'16              LM
000F'2500            CI      0
0011'9404            BNZ     20$
0013'29009A'         JMP     PWCNML           ; Not active - Branch 0016'2503    20$     CI      3                ; Initial Pass ?
0018'9411            BNZ     30$              ; No - Branch
001A'2A0FD3          DCI     PCATMR           ; Yes - Set up Parameters
001D'2002            LI      PCAHON           ;   Power On Time
001F'17              ST
0020'4C              LR      A,S              ;   Get Current Temperature
0021'2408            AI      PCADLT           ;   Add required gain
0023'18              COM                      ;   Form negative for easy checking
0024'1F              INC
0025'17              ST                       ;   Save in PCATMP
0026'72              LIS     2                ;   Set State in PCASTT to Power On
0027'17              ST
0028'9071            BR      PWCNML 002A'65      30$     LISU    TEMPU            ; Has the temperature reached the goal?
002B'68              LISL    TEMPL            ;   Get the current temperature
002C'4C              LR      A,S
002D'2A0FD4          DCI     PCATMP           ;   Add the negative of the goal
0030'88              AM                       ;   Current Temp at or above goal?
0031'8163            BP      70$              ;   Yes - Branch to successfully end test
0033'16              LM                       ;   No  - Get the state again
0034'2A0FD3          DCI     PCATMR           ;   (Point to the timer)
0037'2502            CI      2                ;   Still in first power-on ?
0039'841D            BZ      40$              ;   Yes - Branch
003B'2506            CI      6                ;   Second power on then ?
003D'842C            BZ      50$              ;   Yes - Branch
003F'2501            CI      1                ;   First Wait period ?
0041'843B            BZ      60$              ;   Yes - Branch
0043'16              LM                       ;   No  - Last Wait, Get the timer
0044'24FF            AI      H'FF'            ;   Decrement it
0046'2A0FD3          DCI     PCATMR
0049'17              ST                       ;   Store it back
004A'944F            BNZ     PWCNML           ;   Still Running ? - Branch
004C'16              LM                       ;   No ! - skip over PCATMP
004D'73              LIS     3                ;   -----> Set POA ALARM <-----
004E'17              ST                       ;   Require re-test on restart(PCASTT=3)
004F'64              LISU    LEDU             ;   Set the POA Alarm flag
0050'68              LISL    LEDL
0051'4C              LR      A,S
0052'2201            OI      H'01'
0054'5C              LR      S,A
0055'9044            BR      PWCNML           ;   Keep Power Off 0057   40$     EQU     *                ; First Power-On State
0057'16              LM                       ;   Get the timer
0058'24FF            AI      H'FF'            ;   Decrement it
005A'2A0FD3          DCI     PCATMR           ;   Store it back
005D'17              ST
005E'943B            BNZ     PWCNML           ;   Still running - keep power on
0060'2A0FD3          DCI     PCATMR           ;   Time's up-Set up wait with power off
0063'200A            LI      PCAHOF           ;   (maximum time to wait)
0065'17              ST
0066'16              LM                       ;   (step over PCATMP to PCASTT)
0067'71              LIS     1                ;   State = First Wait
0068'9030            BR      75$ 006A   50$     EQU     *                ; Second Power-On State
006A'16              LM                       ;   Get the timer
006B'24FF            AI      H'FF'            ;   Decrement it
006D'2A0FD3          DCI     PCATMR           ;   Store it back
0070'17              ST
0071'942B            BNZ     PWCNML           ;   Still running - keep power on
0073'2A0FD3          DCI     PCATMR           ;   Time's up-Set up wait with power off
0076'2020            LI      PCAHF2           ;   (maximum time to wait)
0078'17              ST
0079'16              LM                       ;   (step over PCATMP to PCASTT)
007A'75              LIS     5                ;   State = Second Wait
007B'901D            BR      75$ 007D   60$     EQU     *                ; First Wait State
007D'16              LM                       ;   Get the timer
007E'24FF            AI      H'FF'            ;   Decrement it
0080'2A0FD3          DCI     PCATMR
0083'17              ST                       ;   Store it back
```

```
0084'9415              BNZ    PWCNML      ; Still Running ? - Branch
0086'67                LISU   INTG1U      ; Time's up-Clear the integral term to
0087'6E                LISL   INTG1L      ;   overshoot if probe is detected
0088'70                CLR
0089'5D                LR     I,A
008A'5C                LR     S,A
008B'2A0FD3            DCI    PCATMR      ; Set up for second power pulse
008E'2003              LI     PCAHN2      ; Power-On time
0090'17                ST
0091'16                LM                 ; (step over PCATMR to PCASTT)
0092'76                LIS    6           ; State = Second Power-On
0093'9005              BR     75$ 0095'2A0FD5    70$     DCI    PCASTT      ; POA Test Over
0098'70                CLR                ;   Clear the flag
0099'17        75$     ST                 ;   Save the state 009A    PWCNML  EQU    *           ; START NORMAL CALCULATIONS - PROP TERM
009A'1B                EI                 ; * Enable Interrupts *
009B'66                LISU   A11U        ; CLEAR A1
009C'68                LISL   A11L
009D'70                CLR
009E'5D                LR     I,A
009F'5C                LR     S,A
00A0'67                LISU   A21U        ; CLEAR A2
00A1'68                LISL   A21L
00A2'5D                LR     I,A
00A3'5D                LR     I,A
00A4'5D                LR     I,A         ; CLEAR PROP TERM REGISTER
00A5'5C                LR     S,A
00A6'65                LISU   TEMPU       ; CALCULATE PROP TERM
00A7'68                LISL   TEMPL
00A8'4C                LR     A,S         ; GET TEMPERATURE
00A9'18                COM                ; TWOS COMPLIMENT IT
00AA'1F                INC
00AB'65                LISU   TSBINU      ; POINT TO SET POINT
00AC'6B                LISL   TSBINL
00AD'CC                AS     S           ; SUBTRACT Ts - Ta
00AE'67                LISU   A20U        ; 8 BIT DIFFERENCE TO A2
00AF'69                LISL   A20L
00B0'5E                LR     D,A
00B1'8204              BC     POS         ; POS RESULT DO NOTHING
00B3'20FF              LI     H'FF'       ; NEG RESULT, USE TWOS COMPLIMENT
00B5'5C                LR     S,A         ; NEED ONLY COMPLIMENT HIGH BYTE
00B6'66        POS     LISU   A11U
00B7'68                LISL   A11L
00B8'2018              LI     H'18'
00BA'5C                LR     S,A         ; MULT BY 96, TIMES 8 TO SCALE 8 BITS,
00BB'280000$           PI     MMUL        ; TIMES 12 FOR PROP TERM
00BE'66                LISU   A11U
00BF'68                LISL   A11L
00C0'4C                LR     A,S         ; STORE PROP TERM IN PROP1, PROP0
00C1'67                LISU   PROP1U
00C2'6A                LISL   PROP1L
00C3'5C                LR     S,A         ; STORE IN HIGH BYTE
00C4'66                LISU   A10U
00C5'69                LISL   A10L
00C6'4C                LR     A,S
00C7'67                LISU   PROP0U
00C8'6B                LISL   PROP0L
00C9'5C                LR     S,A

*                                  ; CALCULATE INTG TERM PJ
00CA'66                LISU   A11U        ; DIVIDE PROP TERM BY 64
00CB'2006              LI     6           ; SET LOOP COUNTER
00CD'55                LR     S,A
00CE'280000$  DIVPRP   PI     MSR         ; SHIFT RIGHT 1
00D1'4C                LR     A,S         ; EXTEND THE SIGN
00D2'2140              NI     H'40'
00D4'13                SL     1
00D5'EC                XS     S
00D6'5C                LR     S,A
00D7'35                DS     5
00D8'94F5              BNZ    DIVPRP
00DA'65                LISU   TEMPU
00DB'68                LISL   TEMPL       ; DECIDE WHICH TEMPERATURE BAND
00DC'4C                LR     A,S
00DD'18                COM                ; TWOS COMPLIMENT
00DE'1F                INC
00DF'65                LISU   TSBINU
00E0'6B                LISL   TSBINL      ; POINT TO SET POINT
00E1'CC                AS     S           ; SUBTRACT Ts - Ta
00E2'8203              BC     CHKMAG      ; POS, GO CHECK MAGINTUDE
00E4'18                COM                ; NEG, TWOS COMP FIRST
00E5'1F                INC
00E6'21E0     CHKMAG   NI     H'E0'       ; MAGNITUDE GREATER/EQUAL 4 DEG
00E8'943C              BNZ    MININT      ; YES, USE 1/64 Pj, COMPARE TO MIN REG
00EA'66                LISU   A11U        ; NO, MODIFY 1/64 Pj BEFORE COMPARE
00EB'68                LISL   A11L        ; MOVE A1 TO A2
```

```
00EC'4C              LR      A,S
00ED'67              LISU    A21U
00EE'6B              LISL    A21L
00EF'5C              LR      S,A           ; MOVE HIGH BTYE
00F0'66              LISU    A10U
00F1'69              LISL    A10L
00F2'4C              LR      A,S
00F3'67              LISU    A20U
00F4'69              LISL    A20L
00F5'5C              LR      S,A           ; MOVE LOW BYTE
00F6'66              LISU    TPWR1U
00F7'6E              LISL    TPWR1L
00F8'4C              LR      A,S           ; LAST TOTAL POWER TO A1
00F9'66              LISU    A11U
00FA'68              LISL    A11L
00FB'5C              LR      S,A           ; TRANSFER HIGH BYTE
00FC'66              LISU    TPWR0U
00FD'6F              LISL    TPWR0L
00FE'4C              LR      A,S
00FF'66              LISU    A10U
0100'69              LISL    A10L
0101'5C              LR      S,A           ; TRANSFER LOW BYTE
0102'66              LISU    A11U          ; DIVIDE BY 64
0103'2006            LI      6             ; SET LOOP COUNTER
0105'55              LR      S,A
0106'280000$ DIVTPW  PI      MSR           ; SHIFT RIGHT 1
0109'35              DS      5
010A'94FB            BNZ     DIVTPW
010C'280000$         PI      HMUL          ; MULT (1/64)Pp X (1/64)Pt-
010F'66              LISU    A11U          ; MOVE A1 TO A2
0110'6B              LISL    A11L
0111'4C              LR      A,S
0112'67              LISU    A21U
0113'6B              LISL    A21L
0114'5C              LR      S,A           ; TRANSFER HIGH BYTE
0115'66              LISU    A10U
0116'69              LISL    A10L
0117'4C              LR      A,S
0118'67              LISU    A20U
0119'69              LISL    A20L
011A'5C              LR      S,A           ; TRANSFER LOW BYTE
011B'66              LISU    A11U
011C'6B              LISL    A11L
011D'70              CLR
011E'5D              LR      I,A           ; 0.64 TO A1
011F'2029            LI      H'29'
0121'5C              LR      S,A
0122'280000$         PI      HMUL          ; MULT (1/64)Pp X (1/64)Pt- X (.64)

; CAL MAGNITUDE REQUIRED MIN INTG TERM
0125'66      MININT  LISU    A11U
0126'6B              LISL    A11L
0127'4C              LR      A,S           ; SAVE PJ IN PJ1, PJ0
0128'67              LISU    PJ1U
0129'6C              LISL    PJ1L
012A'5C              LR      S,A           ; STORE HIGH BYTE
012B'66              LISU    A10U
012C'69              LISL    A10L
012D'4C              LR      A,S
012E'67              LISU    PJ0U
012F'6D              LISL    PJ0L
0130'5C              LR      S,A           ; STORE LOW BYTE
0131'66              LISU    TPWR1U        ; Pt- TO A2

0132'6E              LISL    TPWR1L
0133'4C              LR      A,S
0134'67              LISU    A21U
0135'6B              LISL    A21L
0136'5C              LR      S,A           ; TRANSFER HIGH BYTE
0137'66              LISU    TPWR0U
0138'6F              LISL    TPWR0L
0139'4C              LR      A,S
013A'67              LISU    A20U
013B'69              LISL    A20L
013C'5C              LR      S,A           ; TRANSFER LOW BYTE
013D'67              LISU    A21U          ; DIVIDE Pt- BY 64
013E'2006            LI      6             ; SET LOOP COUNTER
0140'55              LR      S,A
0141'280000$ DPWR    PI      MSR           ; SHIFT RIGHT 1
0144'35              DS      5
0145'94FB            BNZ     DPWR
0147'66              LISU    A11U
0148'6B              LISL    A11L
0149'70              CLR
014A'5D              LR      I,A
014B'200B            LI      H'0B'
014D'5C              LR      S,A           ; 0.171 TO A1
014E'280000$         PI      HMUL          ; MULT (1/64)Pt- X (.171)
```

```
                                            ; COMPARE MAGNITUDE OF PJ TO MAGNITUDE
              *                             ; OF MINIMUM REQUIRED
              *
0151*67       LISU    PJ1U                  ; PJ TO A2
0152*6C       LISL    PJ1L
0153*4C       LR      A,S
0154*67       LISU    A21U
0155*68       LISL    A21L
0156*5C       LR      S,A                   ; TRANSFER HIGH BYTE
0157*67       LISU    PJ0U
0158*6D       LISL    PJ0L
0159*4C       LR      A,S
015A*67       LISU    A20U
015B*69       LISL    A20L
015C*5C       LR      S,A                   ; TRANSFER LOW BYTE
015D*67       LISU    A21U                  ; GET MAGNITUDE OF PJ
015E*68       LISL    A21L
015F*4C       LR      A,S
0160*2180     NI      H'80'                 ; GET SIGN
0162*8404     BZ      COMPAR                ; POS, GO COMPARE
0164*280000$  PI      MCOM                  ; NEG, TWOS COMPLIMENT TO GET MAGNITUDE

0167*280000$ COMPAR PI MCMP                 ; COMPARE, PJ - MININTG
```

The following assembly language program and hexidecimal code embodied in the E PROM is the routine of FIGS. 3, 4 and 8:

```
              TITLE   PS4
              SUBTTL  PROBE OUT OF AIRWAY
              FORMLN  48
        *     @Copyright 1983 - Travenol Laboratories, Inc

INTERN  POA
              EXTERN  FWCTL

RSECT   PS4

*
        *     PS4 - POA
        *
        *     CHECKS FOR PROBE OUT OF AIRWAY.
        *

0000 POA    EQU     *
0000*1A       DI                             ; *** Disable Interrupts ***
0001*2A0FD5   DCI     PCASTT                 ; PCA/POA Test active ?
0004*16       LM
0005*1B       EI                             ; *** Enable Interrupts ***
0006*2500     CI      0
0008*8404     BZ      '10$
000A*290092*  JMP     NXSECT                 ; Yes - Branch
         000D 10$    EQU     *
000D*64       LISU    LEDU                   ; CHECK ALARMS THAT TURN HEAT OFF
000E*68       LISL    LEDL
000F*4C       LR      A,S
0010*2108     NI      8                      ; CHECK FOR FEED ALARM
0012*944E     BNZ     RESTRT                 ; ALARM SO RESTART
0014*4C       LR      A,S                    ; CHECK FOR PROBE ALARM
0015*2101     NI      1
0017*840A     BZ      TSMTA                  ; NO ALARM, CONTINUE
0019*62       LISU    FPDCTU                 ; ELSE CHK PROBE ALARM FROM OTHER CODE
001A*6A       LISL    FPDCTL
001B*4C       LR      A,S
001C*2120     NI      H'20'
001E*9411     BNZ     DISABL                 ; PROBE ALARM NOT SET BY THIS CODE, DSB
0020*9064     BR      CHKALM                 ; ELSE HOLD ALM UNTIL CLR BY FEED,PROBE 0022*65 TSMTA LISU    TEMPU                  ; CHECK IF IN ACTIVE REGION OF CODE
0023*68       LISL    TEMPL
0024*4C       LR      A,S                    ; GET TEMP
0025*1B       COM                            ; TWOS COMPLIMENT
0026*1F       INC
0027*65       LISU    TSBINU                 ; POINT TO SET POINT
0028*6B       LISL    TSBINL
0029*CC       AS      S                      ; SUBTR Ts-Ta
002A*9205     BNC     DISABL                 ; Ta>Ts DISABLE, OUTSIDE RANGE
002C*24E6     AI      H'E6'                  ; SUBTR 3.125 DEG
002E*820F     BC      PRBOUT                 ; Ts-Ta > 3 DEG, DO ROUTINE
0030*1A DISABL DI                            ; OUTSIDE RANGE, DISABLE ROUTINE
0031*65       LISU    POATMU
0032*6D       LISL    POATML
0033*70       CLR
0034*5C       LR      S,A
0035*62       LISU    FPDCTU                 ; CLEAR TIMER FLAGS
0036*6A       LISL    FPDCTL
0037*4C       LR      A,S
0038*213F     NI      H'3F'
```

```
003A'5C                 LR      S,A             ; CLEAR ENABLE, TIME-OUT FLAGS
003B'1B                 EI
003C'9055               BR      NXSECT          ; GO TO NEXT SECTION

003E'65     PRBOUT      LISU    HPWRSU          ; CHECK IF PROBE OUT OF AIRWAY
003F'6A                 LISL    HPWRSL
0040'4C                 LR      A,S
0041'2120               NI      H'20'           ; CHECK 15 SECOND SAMPLE TIMER DONE
0043'844E               BZ      NXSECT          ; NO, GO TO NEXT SECTION
0045'4C                 LR      A,S             ; CHECK IF ALREADY SAMPLED
0046'2180               NI      H'80'
0048'9449               BNZ     NXSECT          ; SAMPLED, GO TO NEXT SECTION
004A'4C                 LR      A,S             ; ELSE SET SAMPLE FLAG, DO ROUTINE
004B'2280               OI      H'80'
004D'5C                 LR      S,A
004E'62     TMRIN       LISU    FPDCTU          ; CHECK IF FOA TIMER ENABLED
004F'6A                 LISL    FPDCTL
0050'4C                 LR      A,S
0051'2180               NI      H'80'
0053'841A               BZ      RESTR1          ; NO, RESTART 10 MIN TIMER
0055'65                 LISU    TPOASU          ; ELSE CHECK CHANGE IN TEMPERATURE
0056'6C                 LISL    TPOASL          ; GET START TEMP
0057'4C                 LR      A,S
0058'2409               AI      9               ; ADD 1.125 DEG
005A'18                 COM                     ; TWOS COMPLIMENT
005B'1F                 INC
005C'65                 LISU    TEMPU           ; POINT TO CURRENT TEMPERATURE
005D'68                 LISL    TEMPL
005E'CC                 AS      S               ; SUBTR, Tp-(Tst+1.125)

005F'9225               BNC     CHKALM          ; DIFF </= 1 DEG, CHK IF ALARM
0061'62     RESTRT      LISU    FPDCTU          ; RESET PROBE ALM IF SET HERE
0062'6A                 LISL    FPDCTL
0063'4C                 LR      A,S
0064'2120               NI      H'20'
0066'9407               BNZ     RESTR1          ; ALM NOT SET HERE, RESET TIMER ONLY
0068'64                 LISU    LEDU            ; CLEAR PROBE ALARM
0069'68                 LISL    LEDL
006A'4C                 LR      A,S
006B'21FE               NI      H'FE'
006D'5C                 LR      S,A
006E'1A     RESTR1      DI                      ; RESTART FOA TIMER
006F'65                 LISU    POATMU
0070'6D                 LISL    POATML
0071'20EF               LI      239
0073'5C                 LR      S,A
0074'62                 LISU    FPDCTU          ; SET ENABLE FLAG
0075'6A                 LISL    FPDCTL
0076'4C                 LR      A,S
0077'2280               OI      H'80'
0079'21BF               NI      H'BF'           ; CLEAR TIME OUT FLAG
007B'5C                 LR      S,A
007C'1B                 EI
007D'65                 LISU    TEMPU           ; STORE START TEMP
007E'68                 LISL    TEMPL
007F'4C                 LR      A,S
0080'65                 LISU    TPOASU
0081'6C                 LISL    TPOASL
0082'5C                 LR      S,A
0083'900E               BR      NXSECT          ; GO TO NEXT SECTION

0085'62     CHKALM      LISU    FPDCTU          ; CHECK IF ALARM SHOULD BE SET
0086'6A                 LISL    FPDCTL
0087'4C                 LR      A,S             ; TIMER TIMED OUT ?
0088'2140               NI      H'40'
008A'B407               BZ      NXSECT          ; NO, NO ALARM, GO TO NEXT SECTION
008C'64                 LISU    LEDU            ; ELSE SET PROBE ALARM
008D'68                 LISL    LEDL
008E'4C                 LR      A,S
008F'2201               OI      1
0091'5C                 LR      S,A
0092'290000$ NXSECT     JMP     PWCTL           ; GO TO NEXT SECTION
```

The following assembly language program embodied in the E PROM is the decreasing temperature routine of FIGS. 5 and 9:

```
            TITLE   PS6D
            SUBTTL  PROBE-OUT-OF-AIRWAY DOWNSLOPE CHECK
            FORMLN  48
    *       @Copyright 1983 - Travenol Laboratories, Inc

INTERN  PS6D
            EXTERN  PS6BRT

RSECT   PS6D

*
    *       PS6D - FOA DOWNSLOPE
```

```
*      Prevent overtemperature condition resulting from the airway
*      temperature probe falling out of the airway. (Once it's out
*      the system will be measuring room temperature and will cause
*      the power control algorithm to overheat the air.) Note that
*      instead of a true POA Alarm, this module sets the LOW TEMP
*      Alarm.  This is because this code will probably set an alarm
*      during routine circuit change and the Low Temperature Alarm is
*      easier to reset than a POA Alarm.
*
*      Module PS4 also contains a POA check, mainly useful while the
*      system is warming up.  This code simply checks for a drop
*      in temperature, therefore is most useful once the system is at
*      steady-state.  Additionally PS5A contains an 'impulse response'
*      test which runs instead of the PCA on power up.
*
*      Note that this is a '2-stage' check - i.e. a temperature drop
*      must be observed twice in a row before the alarm is set.
*

0001   DWNSLP  EQU    1                    ;;; Conditional Assembly Switch
                                            ;;;   0 = Do NOT Include Test
                                            ;;;   1 = Include Code

LOCAL

0000   PS6D    EQU    *
01             IF     DWNSLP
0000'64        LISU   LEDU                  ;;; Should this check be done ?
0001'68        LISL   LEDL
0002'4C        LR     A,S                   ;;; Get the status
0003'2181      NI     H'81'                 ;;; Don't if 'TEST' or 'POA ALM'
0005'944C      BNZ    50$                   ;;; Not Legal to Run - Branch
0007'2A0FD5    DCI    PCASTT                ;;; Impulse Test Running ?
000A'16        LM
000B'2500      CI     0
000D'9444      BNZ    50$                   ;;; Yes - Branch
000F'2A0FD0    DCI    POATMR                ;;; Check for end of period
0012'16        LM                           ;;; Get the Downcounter
0013'24FF      AI     H'FF'                 ;;; Decrement
0015'2A0FD0    DCI    POATMR
0018'17        ST
0019'944A      BNZ    70$                   ;;; Not counted down yet-Brch 001B'2A0FD2    DCI    POAOLD                ;;; OK, run-Get 'old' probe temp
001E'16        LM
001F'2400      AI     0                     ;;; (set condition codes)
0021'841B      BZ     30$                   ;;; Not active - Branch
0023'18        COM                          ;;; Form the two's complement
0024'1F        INC
0025'65        LISU   TEMPU                 ;;; Add the current temp
0026'68        LISL   TEMPL
0027'CC        AS     S
0028'8214      BC     30$                   ;;; Current Temp Greater-Brnch
002A'2410      AI     POADRP                ;;; Add allowed drop amount
002C'8210      BC     30$                   ;;; Temp diff in range-Branch
002E'64        LISU   LEDU                  ;;; Dropped too much 3 stages
002F'68        LISL   LEDL
0030'4C        LR     A,S
0031'21BF      NI     .NOT.(H'40')          ;;; Make Sure 'Warm-Up' is Off
0033'2202      OI     H'02'                 ;;; *** Set LOW TEMP Alarm ***
0035'5C        LR     S,A
0036'2A0FD1    DCI    POATMP                ;;; Turn off previous Temp
0039'70        CLR
003A'17        ST
003B'9016      BR     50$ 003D   30$    EQU     *              ;;; Normal temperature check
003D'2A0FD1    DCI    POATMP                ;;; Get previous probe temp
0040'16        LM
0041'18        COM                          ;;; Form the two's complement
0042'1F        INC
0043'65        LISU   TEMPU                 ;;; Add current chest temp
0044'68        LISL   TEMPL
0045'CC        AS     S
0046'820B      BC     50$                   ;;; Current Temp Greater-Brnch
0048'2410      AI     POADRP                ;;; Add allowed drop amount
004A'8207      BC     50$                   ;;; Temp diff in range-Branch
004C'2A0FD1    DCI    POATMP                ;;; Drop is noticed-record old
004F'16        LM
0050'9002      BR     55$ 0052   50$    EQU     *              ;;; Reset 'Old' temperature too%
0052'70        CLR
       0053   55$    EQU     *
0053'2A0FD2    DCI    POAOLD
0056'17        ST
       0057   60$    EQU     *              ;;; Reset Data Cells/New period
```

```
0057*2008            LI      POWFER        ;;;  Length of time period
0059*2A0FD0          DCI     POATHR
005C*17              S1
005D*65              LISU    TEMPU         ;;;  Current Probe Temperature
005E*68              LISL    TEMPL
005F*4C              LR      A,S
0060*2A0FD1          DCI     POATMF
0063*17              ST
        0064  70$    EQU     *
                     ENDIF
0064*290000$         JMP     PS6BRT        ;;;  Return to PS6B
```

The following assembly language program and hexidecimal code embodied in the E PROM is the temperature drop routine of FIGS. 6 and 10:

```
          *
          *         Absolute Low Temperature Check
          *
          *         Once the Temperature has risen above a threshold (LOWARM)
          *         if the temperature falls below a certain temperature
          *         (LOWTRG) a Low Temperature Alarm is triggered.
          *
        00C6  NXMOD  EQU     *             ; --- Absolute Low Temperature Check ---
00C6*65              LISU    TEMPU         ; Point to the current temperature
00C7*68              LISL    TEMPL
00C8*1A              DI                    ; *** Disable Interrupts ***
00C9*2A0FD6          DCI     LOWACT        ; Has the threshold been passed ?
00CC*16              LM
00CD*2500            CI      0
00CF*940F            BNZ     30$           ; Yes - Branch
00D1*4C              LR      A,S           ; No  - Check if we have now reached it
00D2*1B              COM                   ; Get -Temperature
00D3*1F              INC
00D4*246F            AI      LOWARM-1      ; Add Threshold Temperature
00D6*8217            BC      50$           ; Not there yet - Branch
00D8*2A0FD6          DCI     LOWACT
00DB*71              LIS     1             ; Remember we've passed this way
00DC*17              ST
00DD*9010            BR      50$
        00DF  30$    EQU     *             ; Check that temperature has not dropped
00DF*4C              LR      A,S           ; too low
00E0*18              COM                   ; Get - Temperature
00E1*1F              INC
00E2*2460            AI      LOWTRG        ; Add Alarm Trigger Temperature
00E4*9209            BNC     50$           ; Not there yet - Branch
00E6*64              LISU    LEDU          ; At or Below Minimum Absolute Temp
00E7*68              LISL    LEDL
00E8*4C              LR      A,S           ; Get the LED Status Cell
00E9*21BF            NI      .NOT.(H'40')  ; Insure Warm-up is off
00EA*2202            OI      H'02'         ; --- Set Low Temperature Alarm
00ED*5C              LR      S,A
        00EE  50$    EQU     *
00EE*1B              EI                    ; *** Enable Interrupts ***
00EF*290000$         JMP     POA           ; GO CHECK PROBE-OUT-OF-AIRWAY
                     END
```

What is claimed is:

1. A process for detecting if a temperature sensor is correctly located in a respiratory type heating conduit at a point that is remote from the heater, which comprises the steps of:
    applying a predetermined amount of power to the heater for a predetermined amount of time, said predetermined amount of time being generally in the range of less than one minute;
    observing any change in the temperature sensed by the temperature sensor within a first fixed time period, said fixed time period being generally in the range of three minutes and occurring after said predetermined amount of time; and
    providing a signal indicating that the temperature is located correctly if the temperature sensed by the temperature sensor has risen at least a predetermined amount.

2. A process as described in claim 1, including the steps of if, during observation, the temperature sensed has not risen at least a predetermined amount, then applying a second predetermined amount of power for a second predetermined amount of time;
    again observing any change in the temperature sensed by the temperature sensor; and
    providing a signal indicating that the temperature sensor is located correctly if the temperature sensed by the temperature sensor has risen at least a predetermined amount.

3. A process as described in claim 2, including the step of providing an alarm signal if the temperature sensed has not risen at least a predetermined amount after the second appplication of power.

4. A process as described in claim 1, including the step of observing any change only when the power is not being applied.

5. A process as described in claim 4, including the step of providing an observation time that is substantially greater than the power application time.

6. A process for detecting if a temperature sensor is correctly located in a respiratory therapy heating conduit at a point that is remote from the heater, which comprises the steps of:
    applying, at successive intervals, predetermined amounts of power to the heater for predetermined amounts of time;

between the power applications, observing any change in the temperature sensed by the temperature sensor; and providing a signal indicating that the temperature sensor is located correctly if the temperature sensed by the temperature sensor has risen at least a predetermined amount.

7. A process as described in claim 6, including the step of providing an alarm signal if the temperature sensed has not risen at least a predetermined amount after a predetermined number of power applications.

8. A process for detecting if a temperature sensor is correctly located in a respiratory therapy heating conduit for delivering gas to a patient at a point that is remote from the heater and adjacent the patient's respiratory system, which comprises the steps of:

storing the sensed temperature;

detecting if the temperature sensed has dropped at least a first predetermined amount within a first predetermined time period;

if the temperature sensed has dropped at least said first predetermined amount within the first predetermined time period, then determining if the temperature remains at this lower level or decreases still more during a second predetermined time period after the temperature drop is detected; and providing an alarm signal only if the temperature remains at this lower level or decreases still more during said second predetermined time period.

9. A process as described in claim 8, wherein said first predetermined amount is 2° C., said first predetermined time period is 20 seconds, and said second predetermined time period is 20 seconds.

10. A process for detecting if a temperature sensor is located in a respiratory therapy heating conduit at a point that is remote from the heater, which comprises the steps of:

applying a predetermined amount of power to the heater for a first predetermined amount of time;

observing any change in the temperature sensed by the temperature sensor;

providing a first signal if the temperature sensed by the temperature sensor has risen at least a first predetermined amount;

detecting if the temperature sensed is at least a second predetermined amount below a selected set point;

if the temperature sensed is at least said second predetermined amount below the selected set point, then setting a time for a second selected amount of time;

observing any change in the temperature sensed during the second selected amount of time;

providing an alarm signal if the temperature sensed has not risen at least a third predetermined amount during the second selected amount of time;

storing the sensed temperature;

detecting if the temperature sensed has dropped at least a fourth predetermined amount within a third predetermined time period;

if the temperature sensed has dropped at least said fourth predetermined amount within said third predetermined time period, then determining if the temperature remains at this lower level or decreases still more during a fourth predetermined time period after the temperature drop is detected; and providing an alarm signal if the temperature does not increase during said fourth predetermined time period.

11. A process for detecting if a temperature sensor is correctly located in a respiratory therapy type heating conduit at a point that is remote from the heater which comprises the steps of:

applying a predetermined amount of power to the heater for a predetermined amount of time;

observing any change in the temperature sensed by the temperature sensor;

providing a signal indicating that the temperature sensor is located correctly if temperature sensed by the temperature sensor has risen at least a predetermined amount;

if during observation, the temperature has not risen at least a predetermined amount, then applying a second predetermined amount of power for a second predetermined amount of time;

again observing any change in temperature sensed by the temperature sensor after said application of said second predetermined amount of power; and dicating that the temperature sensor is providing a signal in located correctly if the temperature sensed by the temperature sensor has risen at least a predetermined amount.

12. A process as described in claim 11, including the step of providing an alarm signal if the temperature sensed has not risen at least a predetermined amount after the second application of power.

* * * * *